United States Patent
Dias et al.

[11] Patent Number: 6,022,381
[45] Date of Patent: Feb. 8, 2000

[54] OXIDATIVE HAIR COLORING COMPOSITIONS WHICH CONTAIN A PREFORMED ORGANIC PEROXYACID OXIDIZING AGENT

[75] Inventors: Louis Carlos Dias; Rowena Juliet Flux Pullan, both of Surrey; Alison Jane Sanger, Farnborough, all of United Kingdom

[73] Assignee: Procter & Gamble Company, Cincinnati, Ohio

[21] Appl. No.: 09/091,441
[22] PCT Filed: Dec. 17, 1996
[86] PCT No.: PCT/US96/20167
  § 371 Date: Jun. 29, 1998
  § 102(e) Date: Jun. 29, 1998
[87] PCT Pub. No.: WO97/24105
  PCT Pub. Date: Jul. 10, 1997

[30] Foreign Application Priority Data

Dec. 29, 1995 [GB] United Kingdom .................... 9526711

[51] Int. Cl.⁷ ...................................................... A61K 7/13
[52] U.S. Cl. ........................................ 8/406; 8/401; 8/431
[58] Field of Search ................................ 8/404, 405, 406, 8/431, 435, 401

[56] References Cited

U.S. PATENT DOCUMENTS

| | | | |
|---|---|---|---|
| 3,251,742 | 5/1966 | Soloway | 8/401 |
| 3,749,674 | 7/1973 | Jones et al. | 8/108.1 |
| 3,861,868 | 1/1975 | Milbrada | 8/410 |
| 4,021,538 | 5/1977 | Yu et al. | 424/60 |

FOREIGN PATENT DOCUMENTS 1465870 1/1967 France .

*Primary Examiner*—Caroline D. Liott
*Attorney, Agent, or Firm*—T. David Reed; Tara M. Rosnell

[57] ABSTRACT

Hair coloring compositions comprise a preformed organic peroxyacid oxidizing agent selected from the group consisting of (i) a compound of the formula

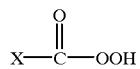

wherein X is a substituted or unsubstituted $C_{12}$ alkyl group, and (ii) a compound of the formula

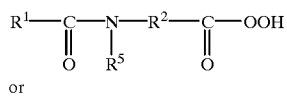

or

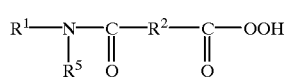

wherein $R^1$ is selected from the group consisting of alkyl, aryl and alkaryl groups with from 1 to 14 carbon atoms, $R^2$ is selected from the group consisting of alkylene, arylene and alkarylene groups containing from 1 to 14 carbon atoms, and $R^5$ is selected from the group consisting of H, alkyl, aryl and alkaryl groups containing 1 to 10 carbon atoms; and at least one oxidative hair coloring agent. The compositions are suitable for coloring human or animal hair and may be provided in a hair coloring kit comprising a single package including two separate bottles.

20 Claims, No Drawings

«6,022,381»

OXIDATIVE HAIR COLORING COMPOSITIONS WHICH CONTAIN A PREFORMED ORGANIC PEROXYACID OXIDIZING AGENT

TECHNICAL FIELD

This invention relates to hair coloring compositions and processes for coloring hair, and more especially to hair coloring compositions comprising at least one preformed organic peroxyacid oxidising agent in combination with one or more oxidative hair coloring agents.

BACKGROUND OF THE INVENTION

The desire to alter the color of human hair is not a facet of modem times. Since the days of the Roman Empire the color of human hair has been routinely altered to accomodate the changes of fashion and style. However the attainment of precise initial colors which are retained by the hair for a desirable period has remained a more elusive goal. The difficulties in the development of hair coloring compositions which can deliver precise long-lasting colors are in part due to the inherent structure of the hair itself and in part due to the necessary conditions of effective hair coloration processes.

In general, the condition and structure of human hair is not regular along the length of the hair shaft. Human hair is subject to various chemical and mechanical treatments such as combing, brushing, shampooing, heating, perming as well as exposure to the sun. As such, the hair at the ends of the hair shaft will generally exhibit signs of damage relative to the new growth close to the scalp. This damage can lead to inconsistent coloration when the hair is dyed due to irregular uptake of the hair coloring agents along the length of the hair shaft. Thus there is a need for hair coloring compositions which can deliver substantially consistent hair color results throughout the hair.

Once the hair has been colored there is a desire for the color to be resistant to the fading action of the sun and other exterior factors and for the color to be retained in a consistant manner for a predictable period of time. Thus it would be desirable to develop a hair coloring composition which exhibited reduced fade and provided improved resistance to wash out during regular cleansing regimen. An additional difficulty commonly associated with the dyeing of human hair is the need for dye systems which avoid any adverse effect on the hair and skin of the user.

Over the years significant effort has been directed towards the elimination of many of the problems associated with the dyeing of human hair. In particular oxidative dyes have been developed which are small molecules which are capable of diffusing into the hair. As detailed later herein these small molecules may then be activated by a peroxide material and react with further molecules to form a larger colored complex in the hair shaft.

To color human or animal hair using oxidative dye technology it is generally necessary to treat the hair with a mixture of suitable oxidative coloring agents and at least one dye oxidising agent. Hydrogen peroxide is the most commonly used dye oxidising agent. However, in addition to dye oxidation, hydrogen peroxide treatment of the hair can also solubilise the colored melanin component in the hair and can lead to undesirable hair qualities, such as poor condition, due to increased brittleness and hair damage. These undesirable qualities are in part due to the necessary conditions of conventional peroxide treatment, as part of the hair coloring process, which requires high pH (>pH 9), extended exposure (from 10 to 60 minutes) and relatively high concentration of oxidising solutions (up to 20% volume of oxygen) in order to deliver effective dye oxidisation. Thus there is a need for hair coloring compositions which can deliver good color in combination with desirable hair conditioning attributes.

Hair coloring compositions containing oxidative dyes, commonly contain, in addition to the dye and a source of peroxide, peroxide activating agents and a variety of additional cosmetic and peroxide stabilising agents. Peroxide dye oxidation agents can oxidise oxidative dyes across a range of pH (pH 2 to 12). However it is known that enhanced dye oxidation can be achieved via the use of a hair swelling agent (HSA) which can adjust the pH of the oxidising solution. Such HSA's further enhance the oxidising and coloring process by swelling the hair fibres to aid both the diffusion of the peroxide and coloring agents into the hair and enabling faster, more thorough dye oxidisation and hair coloring. The preferred HSA for adjusting the pH of peroxide hair oxidising compositions is an aqueous (alkaline) solution containing ammonia (ammonium hydroxide). However ammonia can cause skin irritation when used at levels of about 1% by weight of composition or higher.

Oxidative dyes and peroxide dye oxidising agents can be used to deliver a variety of hair colors to the hair. However such hair coloring compositions comprising oxidative dyes and peroxide dye oxidising agent do not deliver the key consumer needs of color saturation, color vividness, precise initial color predictability, improved wash fastness, improved hair condition and improved safety.

Applicants have now found that hair coloring compositions comprising a combination of preformed peroxy acid oxidising agents with one or more oxidative coloring agents in hair coloring compositions can deliver excellent initial hair color, good wash fastness of the hair color over time as well, desirable color saturation and vividness attributes, and reduced hair damage, are effective at a lower pH and work in a faster time.

Thus it is an object of the present invention to provide fast acting hair coloring compositions.

It is a further object of the present invention to provide hair coloring compositions having improved hair coloring attributes.

It is a further object of the present invention to provide hair coloring compositions which are effective at lower pH.

It is a further object of the present invention to provide hair coloring compositions which impart reduced damage to the hair fibres.

All percentages are by weight of the compositions unless specified otherwise.

SUMMARY OF THE INVENTION

The subject of the present invention is a hair coloring composition suitable for the treatment of human or animal hair.

According to one aspect of the present invention, there is provided a hair coloring composition comprising:

(a) a preformed organic peroxyacid oxidising agent; and (b) one or more oxidative hair coloring agents

DETAILED DESCRIPTION OF THE INVENTION

As used herein the term 'hair' to be treated may be 'living' i.e. on a living body or may be 'non-living' i.e. in a wig, hairpiece or other aggregation of non-living fibres. Mammalian, preferably human hair is preferred. However wool, fur and other melanin containing fibres are suitable substrates for the compositions according to the present invention.

As used herein the term 'hair coloring composition' is used in the broad sense in that it is intended to encompass the combinations herein of preformed organic peroxyacid dye oxidising agent with one or more oxidative coloring agents as well as other ingredients. Moreover, it is also intended to include complex compositions which contain other components which may or may not be active ingredients. Thus, the term 'hair coloring composition' is intended to apply to compositions which contain, in addition to a mixture of active oxidising agents and oxidative coloring agents such things as, by way of example, sequestrants, thickeners, buffers, carriers, surfactants, solvents, antioxidants, polymers non-oxidative dyes and conditioners.

The amount of preformed peroxyacid component in the preferred compositions of the present invention may be expressed both in terms of weight and/or available oxygen' (AO).

The term 'available oxygen', as further defined in the Example section herein, is the theoretical amount of oxygen that can be delivered to the system from the preformed organic peroxyacid oxidising agent. In preferred compositions the total level of available oxygen from the preformed organic peroxyacid is from about 0.5 to about 60, preferably from about 2 to about 55 and especially from about 3 to about 50.

The Dye Oxidisation and Hair Coloring Processes

It is understood by those familiar in the art that to successfully color human or animal hair with oxidative dyes it is generally necessary to treat the hair with a mixture of dye oxidising agent and oxidative dyes. As herein before discussed the dye oxidising agents of the compositions of the present invention are preformed organic peroxyacids.

The mechanisms by which the oxidising agents of the present invention react with oxidative dyes to generate oxidated dye species for hair coloring are not completely understood. A proposed mechanism by which the oxidising agents of the present invention species may interact with primary oxidative dye intermediates and react with couplers to generate colored species is discussed herein under the heading Oxidative Dyes.

Preformed organic peroxyacid

The essential organic peroxyacid oxidising agents of the compositions according to the present invention are, as defined herein, preformed peroxyacids which can be represented by the general formula:

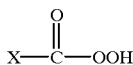

wherein X=substituted or unsubstituted alkyl or aryl group having a preferred average carbon chain length of from $C_1$ to $C_{12}$. Preferred for use herein are preformed organic peroxyacids having carbon chain lengths of $C_1$ and $C_{12}$ respectively, namely peracetic and pernanoic acid. The preformed organic peroxyacids are typically present at a level of from about 0.01% to about 5% by weight, more preferably from about 0.1% to about 4% and especially from about 0.2% to about 3% by weight in the hair coloring compositions of the present invention.

A preferred class of organic peroxyacid compounds are the amide substituted compounds of the following general formulae:

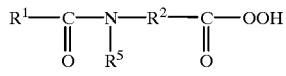

or

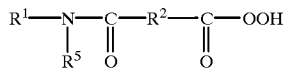

wherein $R^1$ is an alkyl, aryl or alkaryl group with from 1 to 14 carbon atoms, $R^2$ is an alkylene, arylene, and alkarylene group containing from 1 to 14 carbon atoms, and $R^5$ is H or an alkyl, aryl, or alkaryl group containing 1 to 10 carbon atoms. Amide substituted organic peroxyacid compounds of this type are described in EP-A-0,170,386.

Other organic peroxyacids include nonylamidoperoxycaproic acid (NAPCA), diacyl and tetraacylperoxides, especially diperoxydodecanedioc acid, diperoxytetradecanedioc acid and diperoxyhexadecanedioc acid. Mono- and diperazelaic acid, mono- and diperbrassylic acid and N-phthaloylaminoperoxicaproic acid are also suitable herein.

In addition to the essential preformed peroxyacids as outlined above the compositions according to the present invention may optionally contain peroxyacids derived from peroxyacid precursors having the general formula:

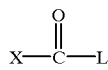

where L is a leaving group and X is essentially any functionality which can facilitate the perhydrolysis reaction and is a poorer leaving group than L, such that upon perhydrolysis the structure of the peroxyacid produced is:

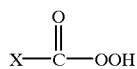

In the mechanism by which peroxyacids are generated from such peroxyacid precursors, it is generally believed that the peroxyacid precursor undergoes nucleophilic attack by a perhydroxyl anion (I), which is generated from deprotonation of the hydrogen peroxide, to form a peroxycarboxylic acid (II). This reaction is commonly referred to as perhydrolysis. A general representation of the perhydrolysis process is illustrated below:

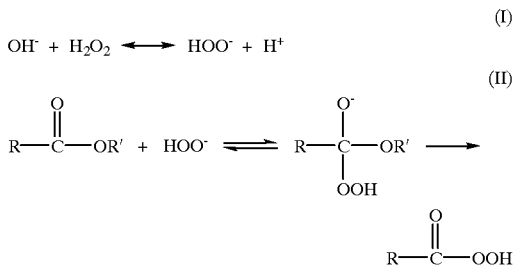

In the above examples R can be an alkyl or aryl group and R' is any suitable leaving group. Suitable examples of R and R' are discussed under the heading Peroxyacid precursor herein. As generation of the perhydroxyl anion (I) from hydrogen peroxide is thought to be the initiating step in the above perhydrolysis process, the maintenance of optimum reaction conditions to promote this conversion is key. Hydrogen peroxide has a pKa in the range of from about 11.2 to about 11.6, and, as such is generally most effective as a oxidising agent at pHs in the range of from about 9 to about 12. In contrast the pKas of the peroxyacid precursors hereinafter detailed are in the range of from about 7 to about 9.5.

Suitable peroxyacid precursor compounds typically contain one or more N- or O-acyl groups in the L position, which precursors can be selected from a wide range of classes. Suitable classes include anhydrides, esters, imides, lactams, enol ethers, sulphonic ester amides and acylated derivatives of imidazoles and oximes. Examples of useful materials within these classes are disclosed in GB-A-1586789. Suitable esters are disclosed in GB-A-836988, 864798, 1147871, 2143231 and EP-A-0170386.

Leaving groups

The leaving group, hereinafter L group, must be sufficiently reactive for the perhydrolysis reaction to occur within the desired time frame (e.g., from 0 to 20 minutes, preferably from 0 to 10 minutes, more preferably from 1 to 5 minutes time exposure).

Preferred L groups are selected from the group consisting of:

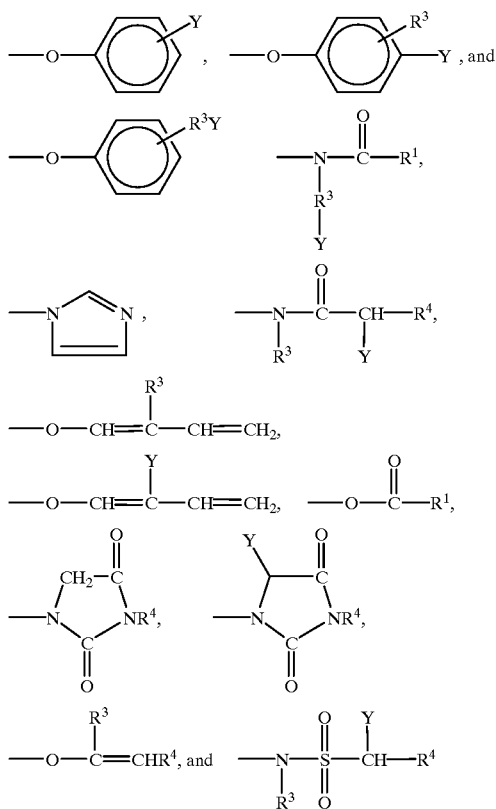

and mixtures thereof, wherein $R^1$ is an alkyl, aryl, or alkaryl group containing from 1 to 14 carbon atoms, $R^3$ is an alkyl chain containing from 1 to 8 carbon atoms, $R^4$ is H or $R^3$, and Y is H or a solubilizing group wherein the solubilizing group is any suitable hydrophilic group capable of enhancing the water solubility of the L group. Any of $R^1$, $R^3$ and $R^4$ may be substituted by essentially any functional group including, for example alkyl, hydroxy, alkoxy, halogen, amine, nitrosyl, amide and ammonium or alkyl ammonium groups.

The preferred solubilizing groups are $—SO_3^{2-}M^+$, $—CO_3^{2-}M^+$, $—SO_4^{2-}M^+$, $—N^+(R^3)_4X^-$ and $O \leftarrow N(R^3)_3$ and most preferably $—SO_3^{2-}M^+$ and $—CO_3^{2-}M^+$ wherein $R^3$ is an alkyl chain containing from 1 to 4 carbon atoms, M is a cation which provides solubility to the precursor aid and X is an anion which provides solubility to the precursor. Preferably, M is an alkali metal, ammonium or substituted ammonium cation, with sodium and potassium being most preferred, and X is a halide, hydroxide, methylsulfate or acetate anion.

A wide variety of peroxyacid precursors may be additionally included in the hair coloring compositions of to the present invention. These include alkyl percarboxylic acid precursors, amide substituted alkyl peroxyacid precursors, perbenzoic acid precursors, cationic peroxyacid precursors, benzoxazin organic peroxyacid precursors.

Alkyl percarboxylic acid precursors

Alkyl percarboxylic acid precursors form percarboxylic acids on perhydrolysis. Preferred precursors of this type provide peracetic acid on perhydrolysis. In general any alkyl percarboxylic precursor having an alkyl carbon chain length of from about 1 to 20 carbon atoms is suitable for use herein. The alkyl chain may be substituted or unsubstituted.

Preferred alkyl percarboxylic precursor compounds of the imide type include the N—,N,N¹N¹ tetra acetylated alkylene diamines wherein the alkylene group contains from 1 to 6 carbon atoms, particularly those compounds in which the alkylene group contains 1, 2 and 6 carbon atoms. Tetraacetyl ethylene diamine (TAED) is particularly preferred.

Other preferred alkyl percarboxylic acid precursors include sodium 3,5,5-tri-methyl hexanonanoyloxybenzene sulfonate (iso-NOB S), sodium nonanoyloxybenzene sulfonate (NOBS), sodium acetoxybenzene sulfonate (ABS) and pentaacetyl glucose. Sodium nonanoyloxybenzene sulfonate is illustrated below:

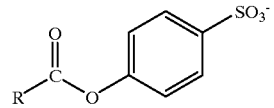

In the above example $R=C_8H_{17}$ wherein $X=C_8H_{17}$ and $L=O—C_6H_4—SO_3—$.

Amide substituted alkyl peroxyacid precursors

Amide substituted alkyl peroxyacid precursor compounds are suitable herein, including those of the following general formulae:

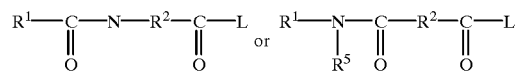

wherein $R^1$ is an alkyl group with from 1 to 14 carbon atoms, $R^2$ is an alkylene group containing from 1 to 14 carbon atoms, and $R^5$ is H or an alkyl group containing 1 to 10 carbon atoms and L can be essentially any leaving group. Amide substituted precursor compounds of this type are described in EP-A-0170386.

Perbenzoic acid precursor

Perbenzoic acid precursor compounds provide perbenzoic acid on perhydrolysis. Suitable O-acylated perbenzoic acid precursor compounds include the substituted and unsubstituted benzoyl oxybenzene sulfonates, and the benzoylation products of sorbitol, glucose, and other saccharides with benzoylating agents, and those of the imide type including N-benzoyl succinimide, tetrabenzoyl ethylene diamine and the N-benzoyl substituted ureas. Suitable imidazole type perbenzoic acid precursors include N-benzoyl imidazole, N-benzoyl caprolactam and N-benzoyl benzimidazole. Other useful N-acyl group-containing perbenzoic acid precursors include N-benzoyl pyrrolidone, dibenzoyl taurine and benzoyl pyroglutamic acid. The example below illustrates N-benzoyl caprolactam:

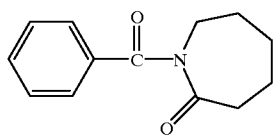

Cationic peroxyacid precursors

Cationic peroxyacid precursor compounds produce cationic peroxyacids on perhydrolysis.

Typically, cationic peroxyacid precursors are formed by substituting the peroxyacid part of a suitable peroxyacid precursor compound with a positively charged functional group, such as an ammonium or alkyl ammonium group, preferably an ethyl or methyl ammonium group. Cationic peroxyacid precursors are typically present in the hair coloring compositions as a salt with a suitable anion, such as a halide ion.

The peroxyacid precursor compound to be so cationically substituted may be a perbenzoic acid, or substituted derivative thereof, precursor compound as described hereinbefore. Alternatively, the peroxyacid precursor compound may be an alkyl percarboxylic acid precursor compound or an amide substituted alkyl peroxyacid precursor as described hereinafter Cationic peroxyacid precursors are described in U.S. Pat. Nos. 4,904,406; 4,751,015; 4,988,451; 4,397,757; 5,269,962; 5,127,852; 5,093,022; 5,106,528; GB-A-1,382,594; EP-A-0,475,512, EP-A-0,458,396 and EP-A-0,284,292; and in JP-A-87-318,332.

Examples of preferred cationic peroxyacid precursors are described in GB-A-9407944.9 and U.S.-A-08/298903; 08/298650; 08/298904 and 08/298906.

Suitable cationic peroxyacid precursors include any of the ammonium or alkyl ammonium substituted alkyl or benzoyl oxybenzene sulfonates, N-acylated caprolactams, and monobenzoyltetraacetyl glucose benzoyl peroxides. Preferred cationic peroxyacid precursors of the N-acylated caprolactam class include the trialkyl ammonium methylene benzoyl caprolactams and the trialkyl ammonium methylene alkyl caprolactams. Illustrated below are examples of an alkyl ammonium substituted benzoyl oxybenzene sulfonate and a trialkyl ammonium methylene benzoyl caprolactam:

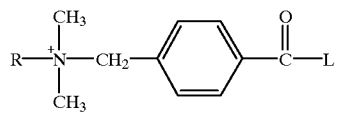

-continued

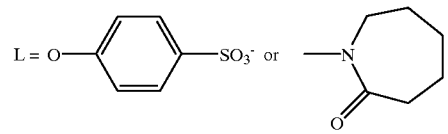

Benzoxazin organic peroxyacid precursors

Also suitable are precursor compounds of the benzoxazin-type, as disclosed for example in EP-A-332,294 and EP-A482,807, particularly those having the formula:

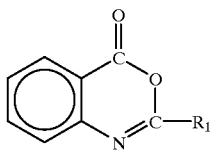

wherein $R_1$ is H, alkyl, alkaryl, aryl, or arylalkyl.

Hair Coloring Agents

The compositions of the present invention include as an essential feature one or more oxididative hair coloring agents. Such oxididative hair coloring agents are used in combination with the oxidising systems of the present invention to formulate permanent, demi-permanent, semi-permanent or temporary hair dye compositions.

Permanent hair dye compositions as defined herein are compositions which once applied to the hair are substantially resistant to wash-out. Demi-permanent hair dye compositions as defined herein are compositions which are substantially removed from the hair after up to 24 washes. Semi-permanent hair dye compositions as defined herein are compositions which once applied to the hair are substantially removed from the hair after up to 10 washes and temporary hair dye compositions as defined herein are compositions which once applied to the hair are substantially removed from the hair after up to 2 washes. Wash out as defined herein is the process by which hair color is removed from the hair over time during normal hair cleansing regimen.

The concentration of each oxidative hair coloring agent in the coloring compositions according to the present invention is from about 0.001% to about 6% by weight and is preferably from about 0.01% to about 2.0% by weight.

The total combined level of oxidative hair coloring agents in the compositions according to the present invention is from about 0.01% to about 15%, preferably from about 0.1% to about 10%, more preferably from about 0.5% to about 5% by weight.

(i) Oxidative dyes

The dye forming intermediates used in oxidative dyes are essentially aromatic diamines, aminophenols and their derivatives. These dye forming intermediates can be classified as; primary and secondary intermediates and nitro dyes. Primary intermediates are chemical compounds which by themselves will form a dye upon oxidation. The secondary intermediates, also known as color modifiers or couplers and are used with other intermediates for specific color effects or to stabilise the color. Nitro dyes are unique in that they are direct dyes which do not require oxidation to dye the hair.

The oxidation dye intermediates which are suitable for use in the compositions and processes herein include aromatic diamines, polyhydric phenols, amino phenols and derivatives of these aromatic compounds ( e.g., N-substituted derivatives of the amines, and ethers of the phenols). Primary oxidation dye intermediates are generally colorless molecules prior to oxidation. The oxidation dye color is generated when the primary intermediate is 'activated' and subsequently enjoined with a secondary intermediate (coupling agent), which is also generally colorless, to form a colored, conjugated molecule.

While not wishing to be bound by any particular theory a representation of the proposed reaction for the activation and coupling is illustrated below wherein the primary dye intermediate (A) is generally understood to be 'activated' (oxidised) by active species (OX) liberated during the decomposition of the preformed organic peroxyacid oxidising agent and/or any additional optional oxidising agents, if present. The 'activated' dye intermediate, which may have structure (B), can then react with a suitable coupler to form a larger 'colored' dye compounds such as dimer and trimers.

thereof, thereby resulting in slight color changes. A representative list of oxidation dye precursors suitable for use herein is found in Sagarin, "Cosmetic Science and Technology","Interscience, Special Edn. Vol 2 pages 308 to 310. It is to be understood that the oxidising aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, amino phenols, and derivatives thereof, described above as primary dye precursors can also have additional substituents on the aromatic ring, e.g. halogen, aldehyde, carboxylic acid, nitro, sulfonic acid and substituted and unsubstituted

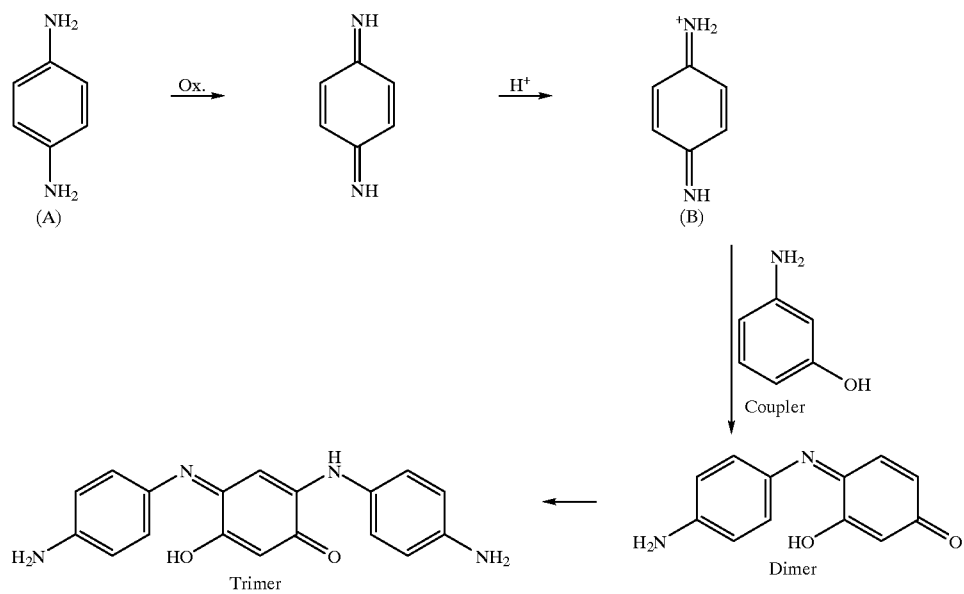

Oxidative dye intermediates diffuse into the hair shaft, which may have been pre-swollen by action of an HSA, if present, and then are activated and coupled to form larger dye complexes within the hair shaft which are less readily washed out.

In general terms, oxidation hair dye precursors or intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidation dye precursors capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Color modifiers (couplers), such as those detailed hereinafter, are preferably used in conjunction with the oxidation dye precursors herein and are thought to interpose themselves in the colored polymers during their formation and to cause shifts in the electronic spectra hydrocarbon groups, as well as additional substituents on the amino nitrogen and on the phenolic oxygen, e.g. substituted and unsubstituted alkyl and aryl groups.

Examples of suitable aromatic diamines, amino phenols, polyhydric phenols and derivatives thereof, respectively, are compounds having the general formulas (VI), (VII) and (VIII) below:

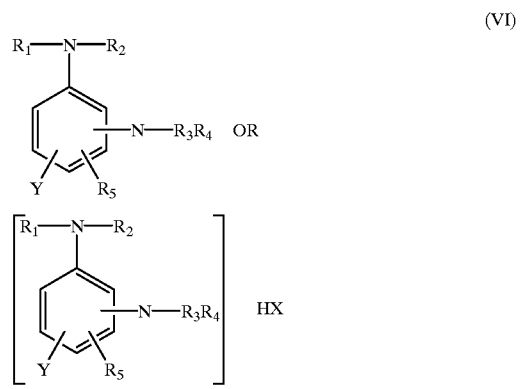

wherein Y is hydrogen, halogen, (e.g. fluorine, chlorine, bromine or iodine), nitro, amino, hydroxyl,

—COOM or —SO$_3$M (where M is hydrogen or an alkali or alkaline earth metal, ammonium, or substituted ammonium wherein one or more hydrogens on the ammonium ion is replaced with a 1 to 3 carbon atom alkyl or hydroxyalkyl radical), wherein $R_1$, $R_2$, $R_3$ and $R_4$ are the same or different from each other and are selected from the group consisting of hydrogen, $C_1$ to $C_4$ alkyl or alkenyl and $C_6$ to $C_9$ aryl, alkaryl aralkyl, and $R_5$ is hydrogen, $C_1$ to $C_4$ unsubstituted or substituted alkyl or alkenyl wherein the substituents are selected from those designated as Y, above, or $C_6$ to $C_9$ unsubstituted or substituted aryl, alkaryl or aralkyl wherein the substituents are selected from those defined as Y, above. Since the precursors of formula (VI) are amines, they can be used herein in the form of peroxide-compatible salts, as noted, wherein X represents peroxide-compatible anions of the type herein before detailed. The general formula of the salt indicated is to be understood to encompass those salts having mono-, di-, and tri-negative anions.

Specific examples of formula (VI) compounds are: o-phenylenediamine, m-phenylenediamine, p-phenylenediamine, 2-chloro-p-phenylenediamine, 2-iodo-p-phenylenediamine, 4-nitro-o-phenylenediamine, 2-nitro-p-phenylenediamine, 1,3,5-triaminobenzene, 2-hydroxy-p-phenylenediamine, 2,4-diamineobenzoic acid, sodium 2,4-diaminobenzoate, calcium di-2,4-, iaminobenzoate, ammonium 2,4-diaminobenzoate, trimethylammonium 2,4-, diaminobenzoate, tri-(2-hydroxyethyl)ammonium 2,4-diaminobenzoate, 2,4-diaminobenzaldehyde carbonate, 2,4-diaminobenzensulfonic acid, potassium 2,4-diaminobenzenesulfonate, N,N-diisopropyl-p-, phenylenediamine bicarbonate, N,N-dimethyl-p-phenylenediamine, N-ethyl-N'-(2-propenyl)-p-phenylenediamine, N-phenyl-p-phenylenediamine, N-phenyl-N-benzyl-p-phenylenediamine, N-ethyl-N-(3-ethylphenyl)-p-phenylenediamine, 2,4-toluenediamine, 2-ethyl-p-phenylenediamine, 2-(2-bromoethyl)-p-phenylenediamine, 2-phenyl-p-phenylenediamine laurate, 4-(2,5-diaminophenyl)benzaldehyde, 2-benzyl-p-phenylenediamine acetate, 2-(4-nitrobenzyl)-p-phenylenediamine, 2-(4-methylphenyl)-p-phenylenediamine, 2-(2,5-diaminophenyl)-5-methylbenzoic acid, methoxyparaphenylenediamine, dimethyl-p-phenylenediamine, 2,5-dimethylpara-phenylenediamine, 2-methyl-5-methoxy-para-phenylenediamine, 2,6-methyl-5-methoxy-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamethyl)aniline, 3-methyl-4-amino-N-ethyl-N-(carbamethyl)aniline, 4-amino-N-ethyl-(β-piperidonoethyl)aniline, 3-methyl-4-amino-N-ethyl-(β-piperidonoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl) aniline, 3-methyl-4-amino-N-ethyl-N-(β-acetylaminoethyl) aniline, 4-amino-N-ethyl-N-(β-mesylaminoethyl) aniline, 3-methyl-4-amino-N-ethyl-N-(β-mesylaminoethyl) aniline, 4-amino-N-ethyl-N-(β-sulphoethyl) aniline, 3-methyl-4-amino-N-ethyl-N-(β-sulphoethyl) aniline, N-(4-aminophenyl)morpholine, N-(4-aminophenyl)piperidine, 2,3-dimethyl-p-phenylenediamine, isopropyl-p-phenylenediamine, N,N-bis-(2-hydroxyethyl)-p-phenylenediamine sulphate.

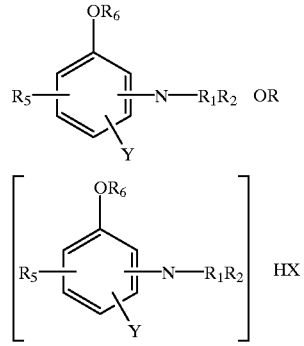

(VII)

where X and Y are the same as in formula (VI), $R_1$ and $R_2$ can be the same or different from each other and are the same as in formula (VI), $R_5$ is the same as in formula (VI) and $R_6$ is hydrogen or $C_1$ to $C_4$ substituted or unsubstituted alkyl or alkenyl wherein the substituents are selected from those defined as Y in formula (VI).

Specific examples of formula (VII) compounds are: o-aminophenol, m-aminophenol, p-aminophenol, 2-iodo-p-aminophenol, 2-nitro-p-aminophenol, 3,4-dihydroxyaniline, 3,4-diaminophenol, chloroacetate, 2-hydroxy-4-aminobenzoic acid, 2-hydroxy-4-aminobenzaldehyde, 3-amino4-hydroxybenzenesulfonic acid, N,N-diisopropyl-p-aminophenol, N-methyl-N-(1 -propenyl)-p-aminophenol, N-phenyl-N-benzyl-p-aminophenol sulphate, N-methyl-N-(3-ethylphenyl)-p-aminophenol, 2-nitro-5-ethyl-p-aminophenol, 2-nitro-5-(2-bromoethyl)-p-aminophenol, (2-hydroxy-5-aminophenyl)acetaldehyde, 2-methyl-p-aminophenol, (2-hydroxy-5-aminophenyl)acetic acid, 3-(2-hydroxy-5-aminophenyl)-1-propene, 3-(2-hydroxy-5-aminophenyl)-2-chloro-1-propene, 2-phenyl-p-aminophenol palmitate, 2-(4-nitrophenyl)-p-aminophenol, 2-benzyl-p-aminophenol, 2-(4-chlorobenzyl-p-aminophenol perchlorate, 2-(4-methylphenyl)-p-aminophenol, 2-(2-amino4-methylphenyl)p-aminophenol, p-methoxyaniline, 2-bromoethyl-4-aminophenyl ether phosphate, 2-nitroethyl-4-aminophenyl ether bromide, 2-aminoethyl4-aminophenyl ether , 2-hydroxyethyl-4-aminophenyl ether, (4-aminophenoxy)acetaldehyde, (4-aminophenoxy)acetic acid, (4-aminophenoxy)methanesulfonic acid, 1-propenyl-4-aminophenyl ether isobutyrate, (2-chloro)-1-propenyl-4-aminophenyl ether, (2-nitro)-1-propenyl-4-aminophenyl ether, (2-amino)-propenyl-4-aminophenyl ether, (2-hydroxy)- 1-propenyl-4-aminophenyl ether, N-methyl-p-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 3-hydroxymethyl-4-aminophenol.

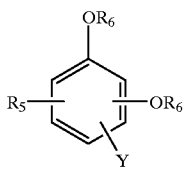
(VIII)

where Y, $R_5$ and $R_6$ are as defined above in formula (VII).

Specific examples of formula (VIII) compounds are: o-hydroxyphenol (catechol), m-hydroxyphenol (resorcinol), p-hydroxyphenol (hydroquinone), 4-methoxyphenol, 2-methoxyphenol, 4-(2-chloroethoxy) phenol, 4-(2-propenoxy) phenol, 4-(3-chloro-2-propenoxy) phenol, 2-chloro-4-hydroxyphenol (2-chlorohydroquinone), 2-nitro-4-hydroxyphenol(2-nitrohydroquinone), 2-amino-4-hydroxyphenol, 1,2,3-trihydroxybenzene (pyrogallol), 2,4-dihydroxybenzaldehyde, 3,4-dihydoxybenzoic acid, 2,4-dihydroxybenzenesulfonic acid, 3-ethyl-4-hydroxyphenol, 3-(2-nitroethyl)-4-hydroxyphenol, 3-(2-propenyl)-4-hydroxyphenol, 3-(3-chloro-2-propenyl)-4-hydroxyphenol, 2-phenyl-4-hydroxyphenol, 2-(4-chlorophenyl) 4hydroxyphenol, 2-benzyl-4-hydroxyphenol, 2-(2-nitrophenyl)4-hydroxyphenol, 2-(2-methylphenyl)-4-hydroxyphenol, 2-(2-methyl-4-chlorophenyl)-4-hydroxyphenol, 3-methoxy-4-hydroxybenzaldehyde, 2-methoxy-4-(1-propenyl)phenol, 4-hydroxy-3-methoxycinnamic acid, 2,5-dimethoxyaniline, 2-methylresorcinol, alpha napthol and salts thereof.

Color modifiers which are suitable for inclusion in the coloring compositions and processes herein before described include certain aromatic amines and phenols and derivatives thereof which do not produce color singly, but which modify the color, shade or intensity of the colors developed by the primary oxidized dye precursors. Certain aromatic amines and phenolic compounds, and derivatives thereof, including some aromatic diamines and polyhydric phenols of the types described by formulas (VI), (VII) and (VIII) above, but which are well known in the art not to be suitable oxidation dye precursors, are suitable as color modifiers herein. Polyhydric alcohols are also suitable for use as color modifiers.

The aromatic amines and phenols and derivatives described above as color modifiers can also have additional substituents on the aromatic ring, e.g., halogen, aldehyde, carboxylic acid, nitro, sulfonyl and substituted and unsubstituted by hydrocarbon groups, as well as additional substituents on the amino nitrogen, or phenolic oxygen, e.g. substituted and unsubstituted alkyl and aryl groups. Again, peroxide-compatible salts thereof are suitable for use herein.

Examples of aromatic amines, phenols and derivatives thereof are compounds of the general formulas (IX) and (X) below:

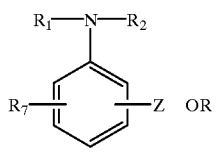
(IX) OR

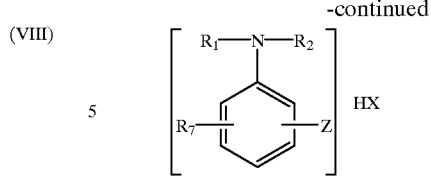
-continued wherein Z is hydrogen, $C_1$ and $C_3$ alkyl, halogen (e.g. fluorine, chlorine, bromine or iodine) nitro,

—COOM or $SO_3M$, (where M is hydrogen or an alkali or alkaline earth metal, ammonium or substituted ammonium wherein one or more hydrogens on the ammonium ion is replaced with a 1 to 3 carbon atom alkyl or hydroxyalkyl radical), wherein $R_1$ and $R_2$ are the same or different and are selected from the group consisting of hydrogen, $C_1$ to $C_4$ alkyl or alkenyl and $C_6$ to $C_9$ aryl, alkaryl or aralkyl and $R_7$ is hydrogen, $C_1$ to $C_4$ unsubstituted or substituted alkyl or alkenyl wherein the substituents are selected from those designated as Z above or $C_6$ to $C_9$ unsubstituted or substituted aryl, alkaryl or aralkyl wherein the substituents are selected from those defined as Z above and wherein X is as defined in formula (VI).

Specific examples of formula (IX) compounds are: aniline, p-chloroaniline, p-fluoroaniline, p-nitroaniline, p-aminobenzaldehyde, p-aminobenzoic acid, sodium-p-aminobenzoate, lithium-p-aminobenzoate, calcium di-p-aminobenzoate, ammonium-p-aminobenzoate, trimethylammonium-p-aminobenzoate, tri(2-hydroxyethyl)-p-aminobenzoate, p-aminobenzenesulfonic acid, potassium p-aminobenzenesulfonate, N-methylaniline, N-propyl-N-phenylaniline, N-methyl-N-2-propenylaniline, N-benzylaniline, N-(2-ethylphenyl)aniline, 4-methylaniline, 4-(2-bromoethyl)aniline, 2-(2-nitroethyl)aniline, (4-aminophenyl)acetaldehyde, (4-aminophenyl)acetic acid, 4-(2-propenyl)aniline acetate, 4-(3-bromo-2-propenyl) aniline, 4-phenylaniline chloroacetate, 4-(3-chlorophenyl) aniline, 4-benzylaniline, 4-(4-iodobenzyl)aniline, 4-(3-ethylphenyl)aniline, 4-(2-chloro-4-ethylphenyl)aniline.

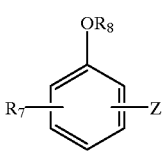
(X)

wherein Z and $R_7$ are defined as in formula (IX) and $R_8$ is hydrogen or $C_1$ to $C_4$ substituted or unsubstituted alkyl or alkenyl wherein the substituents are selected from those defined as Z in formula (IX).

Specific examples of formula (X) compounds are: phenol, p-chlorophenol, p-nitrophenol, p-hydroxybenzaldehyde, p-hydroxybenzoic acid, p-hydroxybenzenesulfonic acid, ethylphenyl ether, 2-chloroethylphenyl ether, 2-nitroethylphenyl ether, phenoxyacetaldehyde, phenoxyacetic acid, 3-phenoxy-1-propene, 3-phenoxy-2-nitro-1-propene, 3-phenoxy-2-bromo-1-propene, 4-propylphenol, 4-(3-bromopropyl)phenol, 2-(2-nitroethyl)phenol, (4-hydroxyphenyl)acetaldehyde, (4-hydroxyphenyl)acetic acid, 4-(2-propenyl)phenol, 4-phenylphenol, 4-benzylphenol, 4-(3-fluoro-2-propenyl)phenol, 4-(4-chlorobenzyl)phenol, 4-(3-ethylphenyl)phenol, 4-(2-chloro-3-ethylphenyl)phenol, 2,5-xylenol, 2,5-diaminopyridine, 2-hydroxy-5-aminopyridine, 2-amino-3-hydroxy pyridine, tetraaminopyrimindine, 1,2,4-trihydroxybenzene, 1,2,4-trihydroxy-5-($C_1$–$C_6$-alkyl)benzene, 1,2,3-trihydroxybenzene, 4-aminoresorcinol, 1,2-dihydroxybenzene, 2-amino-1,4-dihydroxybenzene, 2-amino-4-methoxyphenol, 2,4-diaminophenol, 3-methoxy-1,2-dihydroxy-benzene, 1,4-dihydroxy-2-(N,N-diethylamino)benzene, 2,5-diamino-4-methoxy-1-hydroxybenzene, 4,6-dimethoxy-3-amino-1-hydroxybenzene, 2,6-dimethyl-4-[N-(p-hydroxyphenyl)amino]-1-hydroxybenzene, 1,5-diamino-2-methyl-4-[N-(p-hydroxyphenyl)amino]benzene and salts thereof.

Additional oxidation dye precursors suitable for use herein include catechol species and in particular catechol "dopa" species which includes dopa itself as well as homologs, analogs and derivatives of DOPA. Examples of suitable cachetol species include cysteinyl dopa, alpha alkyl dopa having 1 to 4, preferably 1 to 2 carbon atoms in the alkyl group, epinephrine and dopa alkyl esters having I to 6, preferably 1 to 2 carbon atoms in the alkyl group.

In general suitable catechols are represented by formula (XI) below:

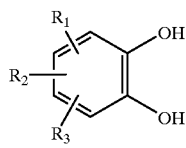

(XI)

wherein $R_1$, $R_2$ and $R_3$, which may be the same or different, are electron donor or acceptor substutuents selected from H, lower ($C_1$–$C_6$) alkyl, OH, OR, COOR, NHCOR, CN, COOH, Halogen, $NO_2$, $CF_3$, $SO_3H$ or $NR_4R_5$, with the proviso that only one of the $R_1$, $R_2$ or $R_3$ can be CN, COOH, halogen, $NO_2$, $CF_3$ or $SO_3H$: $R_4$ and $R_5$, which may be the same or different, are H, lower ($C_1$–$C_6$) alkyl or substituted lower ($C_1$–$C_6$) alkyl in which the substituent may be OH, OR, $NHCOR_6$, $NHCONH_2$, $NHCO_2R_6$, $NHCSNH_2$, CN, COOH, $SO_3H$, $SO_2NR_6$, $SO_2R_6$ or $CO_2R_6$; $R_6$ is lower ($C_1$–$C_6$) alkyl, lower ($C_1$–$C_6$) hydroxyalkyl phenyl linked to the nitrogen by an alkylene chain, phenyl or substituted phenyl with the substituent defined as $R_1$, and R is $C_1$–$C_6$ alkyl or $C_1$–$C_6$ hydroxyalkyl.

The oxidation dye precursors can be used herein alone or in combination with other oxidation dye precursors, and one or more dye precursors can be used in combination with one or more color modifiers. The choice of a single dye precursors and modifiers will be determined by the color, shade and intensity of coloration which is desired. There are nineteen preferred oxidation dye precursors which can be used herein, singly or in combination, to provide oxidation hair dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,N bis (2-hydroxyethyl)p-phenylenediamine, 4-amino-2-hydroxytoluene, 1,5-dihydroxynapthalene and 2,4-diaminoanisole. These can be used in the molecular form or in the form of peroxide-compatible salts, as detailed above.

The primary oxidative dye intermediates and coupling materials as aforementioned herein may be combined to deliver a wide variety of colors to the hair. The hair colors can vary by both depth of color and intensity of color. Intensity of color as defined herein means the quantity of color compound formed on and retained in the hair. In general, high intensity as defined herein means dark or deep colors such as dark red, dark brown or black etc. In accordance, with the above it is possible to formulate hair colors of varying color intensity by adjusting the intial levels of each of the oxidative dyeing materials.

For example low intensity colors such as natural blond to light brown hair shades generally comprise from about 0.001% to about 0.5% by weight of coloring composition of total oxidative dyeing agents and may be acheived by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino)phenyl-ethanol with couplers such as resorcinol, 2-methyl resorcinol or 4-chloro resorcinol.

Similarly combination of the above primary intermediates with 5-amino-2-methylphenol and 1,3-diamino-benzene derivatives such as 2,4-diamino-anisole at levels of from about 0.5% to about 1% of total dyeing agents can lead to medium intensity red colors. High intensity colors such as blue to blue-violet hair shades can be produced by the combination of the above primary intermediates with couplers such as 1,3-diamino-benzene or its derivatives such as 2,5-diamino-toluene at levels of from about 1% to about 6% by weight of composition of total dyeing agents. Black hair colors can be obtained by combining the aforementioned primary intermediates with couplers such as 1,3-diaminobenzene or its derivatives However considerations have been raised against the physiological compatibility of para-amino phenol which is commonly used to impart red colors to the hair. Similarly the physiological compatibility of some of the agents favored for the production of black color such as 1,4-para-diaminobenzene has been called into question. Thus a need exists for oxidative hair coloring compositions which have an improved safety profile and in particular oxidative hair compositions for the delivery of dark colors i.e. high color intensity dyes, which have an improved safety profile.

As hereinbefore described, applicant has found that the combination of the particular preformed organic peroxyacid oxidising agents of the present invention with oxidative dyes is valuable for the provision of both excellent color saturation, vividness and initial coloring attributes. However, applicant has also found that the compositions of the present invention comprising preformed organic peroxyacid precursor oxidising agents with oxidative dyes are valuable for the delivery of good high intensity colors (dark colors) with reduced levels of dye. In particular, applicant has now found that good hair coloring results can be acheived using the dye oxidising systems of the present invention and up to 50% less dye versus conventional hair coloring compositions. As such the compositions according to the present invention are valuable for the delivery of improved hair condition attributes in combination with good intial color and wash fastness over time in addition to having a more accepatable safety profile.

Thus, according to a further aspect of the present invention, there is provided a hair coloring composition comprising:
  (a) from about 0.01% to about 5% by weight of a preformed organic peroxyacid oxidising agent;
  (b) from about 0.0005% to about 3% by weight of one or more oxidative hair coloring agents;

(ii) Non-oxidative and other dyes

The hair coloring compositions of the present invention may, in addition to the essential oxidative hair coloring agents, optionally include non-oxidative and other dye materials. Optional non-oxidative and other dyes suitable for use in the hair coloring compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Edn. by Clarence Robbins (pp250–259); 'The Chemistry and Manufacture of Cosmetics'. Volume IV. 2nd Edn. Maison G. De Navarre at chapter 45 by G. S. Kass (pp841–920); 'cosmetics: Science and Technology' 2nd Edn, Vol II Balsam Sagarin, Chapter 23 by F. E. Wall (pp 279–343); 'The Science of Hair Care' edited by C. Zviak, Chapter 7 (pp 235–261) and .'Hair Dyes', J. C. Johnson, Noyes Data Corp., Park Ridge, U.S.A. (1973), (pp 3–91 and 113–139).

Direct action dyes which do not require an oxidative effect in order to develop the color, are also designated hair tints and have long been known in the art. They are usually applied to the hair in a base matrix which includes surfactant material. Direct action dyes include nitro dyes such as the derivatives of nitroamino benzene or nitroaminophenol; disperse dyes such as nitroaryl amines, aminoanthraquinones or azo dyes; anthraquinone dyes, naphthoquinone dyes; basic dyes such as Acridine Orange C.I. 46005.

Further examples of direct action dyes include the Arianor dyes basic brown 17, C.I.(color index) - no. 12,251; basic red 76, C.I. - 12,245; basic brown 16, C.I. - 12,250; basic yellow 57, C.I. - 12,719 and basic blue 99, C.I. - 56,059 and further direct action dyes such as acid yellow 1, C.I. - 10,316 (D&C yellow no.7); acid yellow 9, C.I. - 13,015; basic violet C.I. - 45,170; disperse yellow 3, C.I. - 11,855; basic yellow 57, C.I. - 12,719; disperse yellow 1, C.I. - 10,345; basic violet 1, C.I. - 42,535, basic violet 3, C.I. - 42,555; greenish blue, C.I. - 42090 (FD&C Blue no.1); yellowish red, C.I.- 14700 (FD&C red no.4); yellow, C.I.19140 (FD&C yellow no5); yellowish orange, C.I.15985 (FD&C yellow no.6); bluish green, C.I.42053 (FD&C green no.3); yellowish red, C.I.16035 (FD&C red no.40); bluish green, C.I.61570 (D&C green no.3); orange, C.I.45370 (D&C orange no.5); red, C.I.15850 (D&C red no.6); bluish red, C.I.15850(D&C red no.7); slight bluish red, C.I.45380(D&C red no.22); bluish red, C.I.45410(D&C red no.28); bluish red, C.I.73360 (D&C red no.30); reddish purple, C.I.17200(D&C red no.33); dirty blue red, C.I.15880(D&C red no.34); bright yellow red, C.I.12085(D&C red no.36); bright orange, C.I.15510(D&C orange no.4); greenish yellow, C.I.47005 (D&C yellow no.10); bluish green, C.I.59040(D&C green no.8); bluish violet, C.I.60730(Ext. D&C violet no.2); greenish yellow, C.I. 10316(Ext. D&C yellow no.7);

Fibre reactive dyes include the Procion (RTM), Drimarene (RTM), Cibacron (RTM), Levafix (RTM) and Remazol (RTM) dyes available from ICI, Sandoz, Ciba-Geigy, Bayer and Hoechst respectively.

Natural dyes and vegetable dyes as defined herein include henna (*Lawsonia alba*), camomile (*Matricaria chamomila* or *Anthemis nobilis*), indigo, logwood and walnut hull extract.

Temporary hair dyes, or hair coloring rinses, are generally comprised of dye molecules which are too large to diffuse into the hair shaft and which act on the exterior of the hair. They are usually applied via a leave-in procedure in which the dye solution is allowed to dry on the hair surface. As such these dyes are typically less resistant to the effects of washing and cleaning the hair with surface active agents and are washed off of the hair with relative ease. Any temporary hair dye may suitably be used in the compositions of the invention and examples of preferred temporary hair dyes are illustrated below.

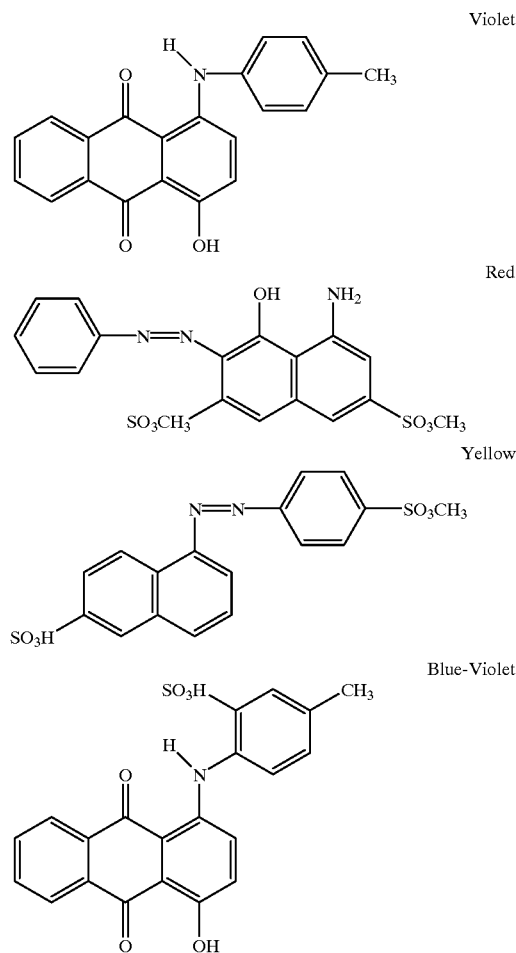

Semi-permanent hair dyes are dyes which are generally smaller in size and effect to temporary hair rinses but are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process and in general semi-permanent dyes are largely washed out of the hair after about 5 to 8 washes. Any semi-permanent dye system may be suitably used in the compositions of the present invention. Suitable semi-permanent dyes for use in the compositions of the present invention are HC Blue 2, HC Yellow 4, HC Red 3, Disperse Violet 4, Disperse Black 9, HC Blue 7, HC Yellow 2, Disperse Blue 3, Disperse violet 1 and mixtures thereof. Examples of semi-permanent dyes are illustrated below:

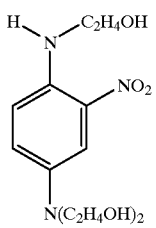

Blue

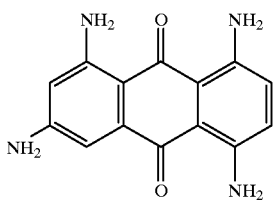

Blue

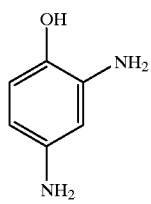

Yellow

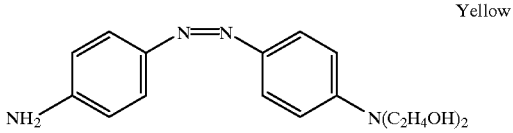

Yellow

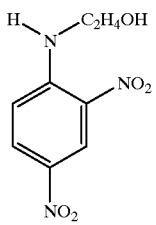

Red

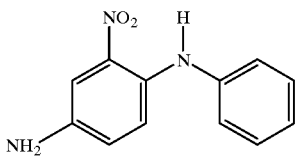

Red

Typical semi-permanent dye systems incorporate mixtures of both large and small color molecules. As the size of the hair is not uniform from root to tip the small molecules will diffuse both at the root and tip, but will not be retained within the tip, while the larger molecules will be generally only be able to diffuse into the ends of the hair. This combination of dye molecule size is used to help give consistent color results from the root to the tip of the hair both during the initial dyeing process and during subsequent washing.

Buffering Agents

The coloring compositions of the present invention have a preferred pH in the range of from about 2 to about 12, more preferably from about 5 to about 10.5, and especially from about 4 to about 9.

As herein before described the preferred coloring compositions of the present invention may contain one or more buffering agents and/or hair swelling agents (HSAs) to adjust the pH to the desired level. Several different pH modifiers can be used to adjust the pH of the final composition or any constituent part thereof.

This pH adjustment can be effected by using well known acidifying agents in the field of treating keratinous fibres, and in particular human hair, such as inorganic and organic acids such as hydrochloric acid, tartaric acid, citric acid, phosphoric acid and carboxylic or sulphonic acids such as ascorbic acid, acetic acid, lactic acid, sulphuric acid, formic acid, ammonium sulphate and sodium dihydrogenphosphate/phosphoric acid, disodium hydrogenphosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Further examples of suitable buffering agents are ammonium hydroxide, ethylamine, dipropylamine, triethylamine and alkanediamines such as 1,3-diaminopropane, anhydrous alkaline alkanolamines such as, mono or di- ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-alginine, lysine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Examples of suitable ion forming compounds are Na2CO3, NaHCO3, K2CO3, (NH4)2CO3, NH4HCO3, CaCO3 and Ca(HCO3) and mixtures thereof.

As herein before described certain alkaline buffering agents such as ammonium hydroxide and monoethylamine (MEA) can also act as hair swelling agents (HSA's).

Preferred for use as a buffering agent for the coloring compositions according to the present invention is ammonium hydroxide.

The coloring compositions according to the present invention may, as will be described later herein, be comprised of a final solution containing both preformed peroxyacid oxidising agent and one or more oxidative hair coloring agents which have been admixed prior to application to the hair. As such, the compositions according to the present invention may comprise coloring kits of a number of separate components and may in addition include optional oxidising agents such as hydrogen peroxide.

In oxidising and coloring kits comprising an additional optional peroxide based oxidising agent such as hydrogen peroxide, which may be present in either solid or liquid form, such as hydrogen peroxide, a buffering agent solution is required to stabilise hydrogen peroxide. Since hydrogen peroxide is stable in the pH range from 2 to 4, it is necessary to use a buffering agent having a pH within this range. Dilute acids are suitable hydrogen peroxide buffering agents. Phosphoric acid is a preferred agent for buffering hydrogen peroxide solutions.

Bleach catalyst

The coloring compositions herein may optionally contain a transition metal containing catalyst for the oxidising agent(s). One suitable type of catalyst is a catalyst system comprising a heavy metal cation of defined bleach catalytic activity, such as copper, iron or manganese cations, an auxiliary metal cation having little or no bleach catalytic activity, such as zinc or aluminium cations, and a sequestrant having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

Other types of suitable catalysts include the manganese-based complexes disclosed in U.S. Pat. No. 5,246,621 and U.S. Pat. No. 5,244,594. Preferred examples of these catalysts include $Mn^{IV}_2(u-O)_3(1,4,7$-trimethyl-1,4,7-triazacyclononane$)_2$-$(PF_6)_2$, $Mn^{III}_2(u-O)_1(u-OAc)_2(1,4,7$-trimethyl-1,4,7-triazacyclononane$)_2$-$(ClO_4)_2$, $Mn^{IV}_4(u-O)_6$ (1,4,7-triazacyclononane$)_4$-$(ClO_4)_2$, $Mn^{III}Mn^{IV}_4(u-O)_1(u$-OAc$)_2$-(1,4,7-trimethyl-1,4,7-triazacyclononane$)_2$-$(ClO_4)_3$, and mixtures thereof.

Others are described in EP-A-0,549,272. Other ligands suitable for use herein include 1,5,9-trimethyl-1,5,9-triazacyclododecane, 2-methyl-1,4,7-triazacyclononane, 2-methyl-1,4,7-triazacyclononane, 1,2,4,7-tetramethyl-1,4,7-triazacyclononane, and mixtures thereof.

For examples of suitable catalysts see U.S. Pat. No. 4,246,612 and U.S. Pat. No. 5,227,084. See also U.S. Pat. No. 5,194,416 which teaches mononuclear manganese (IV) complexes such as $Mn(1,4,7$-trimethyl-1,4,7-triazacyclononane$)(OCH_3)_{3-}(PF_6)$. Still another type of suitably catalyst, as disclosed in U.S. Pat. No. 5,114,606, is a water-soluble complex of manganese (III), and/or (IV) with a ligand which is a non-carboxylate polyhydroxy compound having at least three consecutive C-OH groups. Other examples include binuclear Mn complexed with tetra-N-dentate and bi-N-dentate ligands, including $N_4Mn^{III}(u-O)_2Mn^{IV}N_4)^+$ and $[Bipy_2Mn^{III}(u-O)_2Mn^{IV}bipy_2]-(ClO_4)_3$.

Further suitable catalysts are described, for example, in EP-A-0,408,131 (cobalt complex catalysts), EP-A-0,384,503, and EP-A-0,306,089 (metallo-porphyrin catalysts), U.S. Pat. No. 4,728,455 (manganese/multidentate ligand catalyst), U.S. Pat. No. 4,711,748 and EP-A-0.224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), DE-A-2,054,019 (cobalt chelant catalyst) CA-A-866,191 (transition metal-containing salts), U.S. Pat. No. 4,430,243 (chelants with manganese cations and non-catalytic metal cations), and U.S. Pat. No. 4,728,455 (manganese gluconate catalysts).

Heavy metal ion sequestrant

The coloring compositions of the invention preferably contain as an optional component a heavy metal ion sequestrant. By heavy metal ion sequestrant it is meant herein components which act to sequester (chelate or scavenge) heavy metal ions. These components may also have calcium and magnesium chelation capacity, but preferentially they show selectivity to binding heavy metal ions such as iron, manganese and copper. Such sequestering agents are valuable in hair coloring compositions as herein described for the delivery of controlled oxidising action as well as for the provision of good storage stability of the hair coloring products.

Heavy metal ion sequestrants are generally present at a level of from about 0.005% to about 20%, preferably from about 0.01% to about 10%, more preferably from about 0.05% to about 2% by weight of the compositions.

Various sequestering agents, including the amino phosphonates, available as Dequest (RTM) from Monsanto, the nitriloacetates, the hydroxyethyl-ethylene triamines and the like are known for such use. Suitable heavy metal ion sequestrants for use herein include organic phosphonates, such as the amino alkylene poly (alkylene phosphonates), alkali metal ethane 1-hydroxy disphosphonates and nitrilo trimethylene phosphonates.

Preferred among the above species are diethylene triamine penta (methylene phosphonate), ethylene diamine tri (methylene phosphonate) hexamethylene diamine tetra (methylene phosphonate) and hydroxyethylene 1,1 diphosphonate.

Preferred biodegradable non-phosphorous heavy metal ion sequestrants suitable for use herein include nitrilotriacetic acid and polyaminocarboxylic acids such as ethylenediaminotetracetic acid, ethylenetriamine pentaacetic acid, ethylenediamine disuccinic acid, ethylenediamine diglutaric acid, 2-hydroxypropylenediamine disuccinic acid or any salts thereof. Especially preferred is ethylenediamine-N,N'-disuccinic acid (EDDS). see U.S. Pat. No. 4,704,233, or the alkali metal, alkaline earth metal, ammonium, or substituted ammonium salts thereof, or mixtures thereof.

Other suitable heavy metal ion sequestrants for use herein are iminodiacetic acid derivatives such as 2-hydroxyethyl diacetic acid or glyceryl imino diacetic acid, described in EP-A-317,542 and EP-A-399,133. The iminodiacetic acid-N-2-hydroxypropyl sulfonic acid and aspartic acid N-carboxymethyl N-2-hydroxypropyl-3-sulfonic acid sequestrants described in EP-A-516,102 are also suitable herein. The β-alanine-N,N'-diacetic acid, aspartic acid-N,N'-diacetic acid, aspartic acid-N-monoacetic acid and iminodisuccinic acid sequestrants described in EP-A-509,382 are also suitable.

EP-A-476,257 describes suitable amino based sequestrants. EP-A-510,331 describes suitable sequestrants derived from collagen, keratin or casein. EP-A-528,859 describes a suitable alkyl iminodiacetic acid sequestrant. Dipicolinic acid and 2-phosphonobutane-1,2,4-tricarboxylic acid are also suitable. Glycinamide-N,N'-disuccinic acid (GADS), ethylenediamine-N-N'-diglutaric acid (EDDG) and 2-hydroxypropylenediamine-N-N'-disuccinic acid (HPDDS) are also suitable.

The heavy metal ion sequestering agents of the present invention may be used in their alkali or alkaline earth metal salts.

Thickeners

The coloring compositions of the present invention may additionally include a thickener at a level of from about 0.05% to about 20%, preferably from about 0.1 % to about 10%, more preferably from about 0.5% to about 5% by weight. Thickening agents suitable for use in the compositions herein are selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer which are available from Rohm and Haas, Philadelphia, Pa., U.S.A. Additional thickening agents suitable for use herein include sodium alginate or gum arabic, or cellulose derivatives, such as methyl cellulose or the sodium salt of carboxymethylcellulose or acrylic polymers.

Solvents

Water is the preferred principal diluent for the compositions according to the present invention. As such, the compositions according to the present invention may include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

Enzyme

A further additional material useful in the hair coloring compositions according to the present invention is one or more enzymes.

Suitable enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139 incorporated herein by reference.

Peroxidases are haemoproteins specific for peroxide, but using a wide range of substances as donors. Catalase which decomposes peroxide, is included here in view of the fact that it is generally similar in structure and properties and is able to bring about certain oxidations by $H_2O_2$. The decomposition of $H_2O_2$ can be regarded as the oxidation of one molecule by the other. It is widespread in aerobic cells and may have some more important function. The coenzyme peroxidases are not haemoproteins and one at least is a flavoprotein. Other flavoproteins such as xanthine oxidase will also use $H_2O_2$ among other acceptors, and the coenzyme peroxidases resemble these rather than the classical peroxidases in not being specific for $H_2O_2$. Suitable peroxidases for the compositions of the present invention include horseradish peroxidase, Japanese radish peroxidase, cow's milk peroxidase, rat liver peroxidase, linginase and haloperoxidase such as chloro- and bromo-peroxidase.

Enzymes are optionally incorporated at levels sufficient to provide up to about 50 mg by weight, more typically about 0.01 mg to about 10 mg of active enzyme per gramm of the hair treatment composition of the invention. Stated otherwise the peroxidase enzyme may be incorporated into the compositions in accordance with the invention at a level of from about 0.0001% to about 5%, preferably from about 0.001% to about 1%, more preferably from about 0.01 % to about 1% active enzyme by weight of the composition.

Commercially available protease enzymes include those sold under the trade names Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Protease enzyme may be incorporated into the compositions in accordance with the invention at a level of from 0.0001% to 4% active enzyme by weight of the composition.

Amylases include, for example, α-amylases obtained from a special strain of *B licheniformis,* described in more detail in GB-1,269,839 (Novo). Preferred commercially available amylases include for example, those sold under the tradename Rapidase by Gist-Brocades, and those sold under the tradename Termamyl and BAN by Novo Industries A/S. Amylase enzyme may be incorporated into the composition in accordance with the invention at a level of from 0.0001% to 2% active enzyme by weight of the composition.

Lipolytic enzyme may be present at levels of active lipolytic enzyme of from 0.0001% to 2% by weight, preferably 0.001% to 1% by weight, most preferably from 0.001% to 0.5% by weight of the compositions.

The lipase may be fungal or bacterial in origin being obtained, for example, from a lipase producing strain of Humicola sp., Thermomyces sp. or Pseudomonas sp. including *Pseudomonas pseudoalcaligenes* or *Pseudomas fluorescens.* Lipase from chemically or genetically modified mutants of these strains are also useful herein. A preferred lipase is derived from *Pseudomonas pseudoalcaligenes,* which is described in Granted European Patent, EP-B-0218272.

Another preferred lipase herein is obtained by cloning the gene from *Humicola lanuginosa* and expressing the gene in *Aspergillus oryza,* as host, as described in European Patent Application, EP-A-0258 068, which is commercially available. from Novo Industri A/S, Bagsvaerd, Denmark, under the trade name Lipolase. This lipase is also described in U.S. Pat. No. 4,810,414, Huge-Jensen et al, issued Mar. 7, 1989.

Surfactant Materials

The compositions of the present invention can additionally contain a surfactant system. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

(i) Anionic Surfactants

Anionic surfactants suitable for inclusion in the compositions of the invention include alkyl sulphates, ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$–$C_{22}$, preferably $C_{12}$–$C_{18}$ more preferably $C_{12}$–$C_{14}$.

(ii) Nonionic Surfactants

The compositions of the invention can also comprise a water-soluble nonionic surfactants. Surfactants of this class include $C_{12}$–$C_{14}$ fatty acid mono-and diethanolamides, sucrose polyester surfactants and polyhydroxy fatty acid amide surfactants having the general formula below.

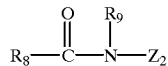

The preferred N-alkyl, N-alkoxy or N-aryloxy, polyhydroxy fatty acid amide surfactants according to the above formula are those in which $R_8$ is $C_5$–$C_{31}$ hydrocarbyl, preferably $C_6$–$C_{19}$ hydrocarbyl, including straight-chain and branched chain alkyl and alkenyl, or mixtures thereof and $R_9$ is typically $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or polysaccharide, and alkoxylated derivatives thereof As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C6–C19 straight chain alkyl or alkenyl group. In compounds of the above formula, $R_8$—CO—N< can be, for example, cocoamide, stearamide, oleamide, lauramide, myristamide, capricamide, palmiamide, tallowamide, etc.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula below:

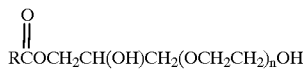

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable polyethoxylated glyceryl fatty ester surfactants include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as evening primrose oil, palm oil, hydrogenated castor oil, almond oil, and corn oil.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant, Suitable polyethylene glycol based polyethoxylated $C_9$–$C_{15}$ fatty alcohols suitable for use herein include $C_9$–$C_{11}$ Pareth-3, $C_9$–$C_{11}$ Pareth4, $C_9$–$C_{11}$ Pareth-5, $C_9$–$C_{11}$ Pareth-6, $C_9$–$C_{11}$ Pareth-7, $C_9$–$C_{11}$ Pareth-8, $C_{11}$–$C_{15}$ Pareth-3, $C_{11}$–$C_{15}$ Pareth-4, $C_{11}$–$C_{15}$ Pareth-5, $C_{11}$–$C_{15}$ Pareth-6, $C_{11}$–$C_{15}$ Pareth-7, $C_{11}$–$C_{15}$ Pareth-8, $C_{11}$–$C_{15}$ Pareth-9, $C_{11}$–$C_{15}$ Pareth-10, $C_{11}$–$C_{15}$ Pareth-11, $C_{11}$–$C_{15}$ Pareth-12, $C_{11}$–$C_{15}$ Pareth-13 and $C_{11}$–$C_{15}$ Pareth-14. PEG 40 hydrogenated castor oil is commercially available under the tradename Cremophor (RTM) from BASF. PEG 7 glyceryl cocoate and PEG 20 glyceryl laurate are commercially available from Henkel under the tradenames Cetiol (RTM) HE and Lamacit (RTM) GML 20 respectively. $C_9$–$C_{11}$ Pareth-8 is commercially available from Shell Ltd under the tradename Dobanol (RTM) 91-8. Particulary preferred for use herein are polyethylene glycol ethers of ceteryl alcohol such as Ceteareth 25 which is available from BASF under the trade name Cremaphor A25.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include:

(a) imidazolinium surfactants of formula (XII)

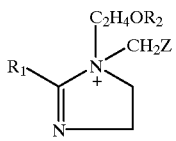

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (XIII)

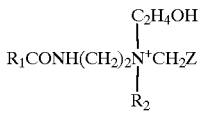

wherein $R_1$, $R_2$ and Z are as defined above;

(b) aminoalkanoates of formula (XIV)

iminodialkanoates of formula (XV)

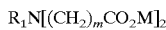

and iminopolyalkanoates of formula (XVI)

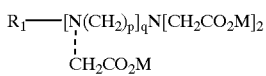

wherein n, m, p, and q are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula (XII), although the CTFA Cosmetic Ingredient Dictionary, 3rd Edition indicates the non-cyclic structure (XIII) while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula XII and/or XIII in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals). Further examples of amphoteric surfactants suitable for use herein include Octoxynol-1 (RTM), polyoxethylene (1) octylphenyl ether; Nonoxynol-4 (RTM), polyoxyethylene (4) nonylphenyl ether and Nonoxynol-9, polyoxyethylene (9) nonylphenyl ether.

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethy-lamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

(iv) Zwitterionic Surfactants

Water-soluble auxiliary zwitterionic surfactants suitable for inclusion in the compositions of the present invention include alkyl betaines of the formula $R_5R_6R_7N^+$ $(CH_2)_n$ $CO_2M$ and amido betaines of the formula (XV) below:

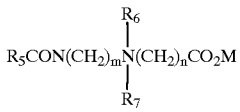

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoa-midopropyldimethylcarboxymethyl betaine, laurylami-dopropyldimethylcarboxymethyl betaine and Tego betaine (RTM).

Water-soluble auxiliary sultaine surfactants suitable for inclusion in the compositions of the present invention include alkyl sultaines of the formula (XVI) below:

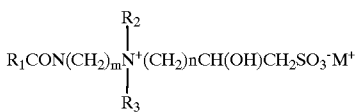

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XVII) below:

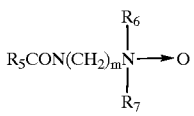

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoa-midopropylamine oxide, lauryl dimethyl amine oxide and myristyl dimethyl amine oxide.

Optional Materials

A number of additional optional materials can be added to the coloring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercapatans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and p-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., U.S.A. and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; hair conditioning agents such as silicones, higher alcohols, cationic polymers and the like; enzyme stabilisers such as water soluble sources of calcium or borate species; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. and water softening agents such as sodium citrate. Water is also present at a level preferably of from about 2% to about 99.9%, preferably from about 5% to about 99%, more preferably at least from about 10% to about 95% and especially from about 15% to 90% by weight of the compositions herein.

The present invention is represented by the following non-limiting examples. In the examples, all concentrations are on a 100% active basis and all percentages are by weight unless otherwise stated and the abbreviations have the following designations:

| | |
|---|---|
| Oxidising agent 1 | peracetic acid |
| Oxidising agent 2 | pernanoic acid |
| Oxidative Dye 1 | para-phenylene diamine |
| Oxidative Dye 2 | para-aminophenol |
| Oxidative Dye 3 | meta-aminophenol |
| Oxidative Dye 4 | 2-amino-3-hydroxy pyridine |
| Non-oxidative Dye 1 | Basic red 76 |
| Non-oxidative Dye 2 | Basic brown 16 |
| Chelating agent | Ethylenediamine tetraaceticacid |
| Enzyme | Horseradish peroxidase |
| Surfactant 1 | Cetereth-25 |
| Surfactant 2 | Cocoamidopropyl betaine |
| Surfactant 3 | Sodium lauryl sulphate |
| Thickener 1 | Cetyl alcohol |
| Thickener 2 | Stearyl alcohol |
| Antioxidant | Sodium sulphite |

Examples I–VI

The following are hair treatment compositions in the form of hair coloring compositions which are representative of the present invention.

In the examples, water is used as a common solvent, however water can be replaced, in part, by up to about 50% by liquids such as lower alcohols, e.g., ethylene glycol, ethylene glycol monoethyl ether, diethylene glycol, diethylene glycol monoethyl ether, propylene glycol, 1,3-propane diol, ethanol, isopropyl alcohol, glycerine, butoxyethanol, ethoxydiglycol, hexylene glycol, polyglyceryl-2-oleyl ether and mixtures thereof.

| Ingredient | I | II | III | IV | V | VI |
|---|---|---|---|---|---|---|
| Oxidising Agent 1 | 0.5 | 1 | 1.5 | — | — | — |
| Oxidising Agent 2 | — | — | — | 0.5 | 1 | 1.5 |
| Oxidative Dye 1 | 0.24 | — | 0.3 | 0.4 | 0.2 | 0.3 |
| Oxidative Dye 2 | 0.09 | 0.05 | 0.12 | 0.09 | 0.06 | 0.06 |
| Oxidative Dye 3 | 0.06 | 0.05 | 0.03 | 0.06 | 0.06 | — |
| Oxidative Dye 4 | 0.06 | 0.05 | 0.05 | 0.06 | 0.03 | — |
| Non-Oxidative Dye 1 | — | 0.25 | — | — | 0.12 | — |
| Non-Oxidative Dye 2 | — | 0.35 | — | — | 0.2 | — |
| Enzyme | — | — | 0.5 | — | — | — |
| Surfactant 1 | 1.5 | 1 | 3 | — | 1 | 1 |
| Surfactant 2 | — | 2 | 1 | 2 | 0.5 | — |
| Surfactant 3 | — | 1 | 0.5 | 1 | — | 2 |
| Chelating agent | 0.1 | 0.1 | 0.1 | 0.1 | 0.1 | 0.1 |
| Thickener 1 | 2.3 | 2.3 | 2.3 | 2.3 | 2.3 | 2.3 |
| Thickener 2 | 2.3 | 2.3 | 2.3 | 2.3 | 2.3 | 2.3 |
| Antioxidant | 0.1 | 0.1 | 0.1 | 0.1 | 0.1 | 0.1 |
| Water | ... to balance ... | | | | | |

Available Oxygen Method

As herein before described the oxidising efficacy of the dye oxidising agents of the coloring compositions of the present invention can be described in terms of their level of 'available oxygen', also referred to as 'active oxygen (AO).

Peroxygen compounds contain the peroxide linkage (—O—O—) in which one of the oxygen atoms is active. This activity can be measured by the oxidation of iodide to iodine under acidic conditions or by a ceric sulphate titration. AO content, usually expressed as a percent, is the atomic weight of active oxygen divided by the molecular weight of the compound. The calculation for determining the theoretical available oxygen from any particular compound is as follows:

$$AO,\% = 100 \times (\text{no. of active oxygens}) \times (16/\text{mol wt of compound})$$

The theoretical levels of available oxygen for peracetic acid, a preformed peroxyacid according to the present invention versus a conventional, hydrogen peroxide, oxidising agent are 21 and 47 respectively.

Method of Manufacture

Many of the preformed organic peroxyacids useful in the coloring compositions of the present invention are unstable, particularly in aqueous solution. It is therefore important to employ these solutions within a short period of time after their preparation in order to achieve the desired oxidation effect to the hair. Furthermore, it is important that the preformed organic peroxyacid be in a form which is easy and convenient to prepare and use by the consumer, since the oxidising agent must remain in contact with the hair for a certain period of time and not run or drip off of the hair, possibly causing eye or skin irritation.

To address the above the coloring compositions of the present invention can be provided in kit form as separately packaged components to maintain stability, and, if so desired, mixed by the user immediately prior to application to the hair. One component of the kit comprises an individually packaged preformed peroxyacid oxidising component. Further kit components could comprise either an individually packaged preformed peroxyacid oxidising aid and coloring agent mixture or two separate individual packages of preformed peroxyacid oxidising aid and coloring agents. In one embodiment of the present invention the oxidising component comprises a preformed organic peroxy acid in an amount such that the final concentration of the compound for use on the hair is from about 0.05% to about 5% by weight and/or additional agents as herein before described and a second component comprises a mixture of suitable coloring agents. The compositions can either be mixed by the user immediately prior to application to the hair or can be applied separately. An example of such a kit is as follows:

A hair coloring kit is assembled comprising a single package including therein: (1) a 50 ml bottle containing a solution of preformed organic peroxyacid oxidising agent and (2) a 50 ml bottle containing one or more oxidative hair coloring agents and additional agents such as surfactants, antioxidants, thickeners etc. The coloring kit may also comprise as an additional optional component (3) a 50 ml bottle of hydrogen peroxide (10% by weight of $H_2O_2$). The oxidative hair coloring agents can be applied to the hair to initiate the hair coloring process and the preformed peroxyacid solution (and additional agents such as peroxide if present) can be applied to the hair either at the same time; imediately afterwards or up to 20 minutes after treatment of the hair with the coloring mixture.

Method of Use

The compositions herein described are used to color hair. The coloring compositions herein are applied to the hair for periods of from 1 minute to 60 minutes depending upon the degree of coloring required. A preferred time is between 5 minutes and 30 minutes.

The products provide excellent hair coloring and in-use efficacy benefits including reduced hair damage at lower pH.

We claim:

1. An oxidative hair coloring composition, comprising
   (a) a preformed organic peroxyacid oxidizing agent selected from the group consisting of (i) a compound of the formula

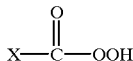

wherein X is a substituted or unsubstituted $C_{12}$ alkyl group, and (ii) a compound of the formula

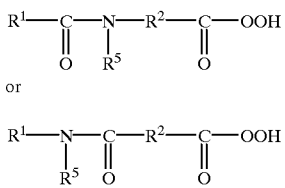

wherein $R^1$ is selected from the group consisting of alkyl, aryl and alkaryl groups with from 1 to 14 carbon atoms, $R^2$ is selected from the group consisting of alkylene, arylene and alkarylene groups containing from 1 to 14 carbon atoms, and $R^5$ is selected from the group consisting of H, alkyl, aryl and alkaryl groups containing 1 to 10 carbon atoms; and
   (b) at least one oxidative hair coloring agent in an amount effective to color hair.

2. A composition according to claim 1, wherein the preformed organic peroxyacid oxidizing agent is of the formula (i).

3. The composition of claim 1, wherein the preformed peroxyacid oxidizing agent is present at a level of from about 0.01% to about 5% by weight of the total composition.

4. The composition of claim 1 wherein the preformed peroxyacid oxidizing agent is present at a level of from about 0.1% to about 4% by weight of the total composition.

5. The composition of claim 1, wherein the preformed peroxyacid oxidizing agent is present at a level of from about 0.2% to about 3% by weight of the total composition.

6. The composition of claim 1, wherein each hair coloring agent is present at a level of from about 0.001% to about 6% by weight.

7. The composition of claim 1, wherein each hair coloring agent is present at a level of from about 0.01% to about 2% by weight.

8. The composition of claim 1, wherein the total level of hair coloring agents is from about 0.01% to about 15% by weight.

9. The composition of claim 8, wherein the total level of hair coloring agents is from about 0.1% to about 10% by weight.

10. The composition of claim 9, wherein the total level of hair coloring agents is from about 0.5% to about 5% by weight.

11. The composition of claim 1, additionally comprising one or more buffering and/or hair swelling agents.

12. The composition of claim 11, wherein the buffering agent is selected from the group consisting of ammonium hydroxide, ethylamine, dipropylamine, triethylamine, alkanediamines, alkanolamines, polyalkylene polyamines, heterocyclic amines, hydroxides of alkali metals, hydroxides of alkali earth metals, basic amino acids, $Na_2CO_3$, $NaHCO_3$, $K_2CO_3$, $(NH_4)_2CO_3$, $NH_4HCO_3$, $CaCO_3$, $Ca(HCO_3)_2$, and mixtures thereof.

13. The composition of claim 1, additionally comprising one or more surfactants.

14. The composition of claim 1, additionally comprising an enzyme.

15. A process for coloring human or animal hair, comprising applying to the hair the oxidative hair coloring composition of claim 1.

16. The process of claim 15, wherein the oxidative hair coloring composition comprises:
    (a) from about 0.01% to about 5% by weight of the preformed organic peroxy acid ozidizing agent;
    (b) from about 0.001% to about 6% by weight of each oxidative hair coloring agent; and
    (c) from about 15% to about 99.9% by weight of an inert diluent, and further wherein the coloring composition has a pH of from about 4 to about 9.

17. An oxidative hair coloring kit, comprising a single package and including therein the combination of: (1) a 50 ml bottle containing a solution of preformed organic peroxyacid oxidizing agent selected from the group consisting of (i) a compound of the formula

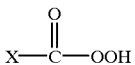

wherein X is a substituted or unsubstituted $C_{12}$ alkyl group, and (ii) a compound of the formula

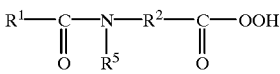

or

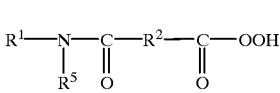

wherein $R^1$ is selected from the group consisting of alkyl, aryl and alkaryl groups with from 1 to 14 carbon atoms, $R^2$ is selected from the group consisting of alkylene, arylene and alkarylene groups containing from 1 to 14 carbon atoms, and $R^5$ is selected from the group consisting of H, alkyl, aryl and alkaryl groups containing 1 to 10 carbon atoms; and (2) a 50 ml bottle containing at least one oxidative hair coloring agent in an amount effective to color hair.

18. An oxidative hair coloring composition, comprising
   (a) from about 0.01% to about 5% by weight of the total composition of a preformed organic peroxyacid oxidizing agent comprising pernanoic acid; and
   (b) at least one oxidative hair coloring agent in an amount effective to color hair.

19. The composition of claim 2, wherein the preformed peroxyacid oxidizing agent is present at a level of from about 0.2% to about 3% by weight of the total composition.

20. The composition of claim 19, wherein the total combined level of hair coloring agents is from about 0.5% to about 5% by weight.

* * * * *